(12) United States Patent
Wada et al.

(10) Patent No.: US 6,432,095 B1
(45) Date of Patent: Aug. 13, 2002

(54) WATER-DECOMPOSABLE ABSORBENT ARTICLE

(75) Inventors: Mitsuhiro Wada; Nobuhiro Kurata; Megumi Tokumoto, all of Kagawa (JP)

(73) Assignee: Uni-Charm Corporation, Ehime (JP)

( * ) Notice: Subject to any disclaimer, the term of this patent is extended or adjusted under 35 U.S.C. 154(b) by 73 days.

(21) Appl. No.: 09/707,390

(22) Filed: Nov. 7, 2000

(30) Foreign Application Priority Data

Nov. 19, 1999 (JP) ............................................. 11-329250

(51) Int. Cl.[7] ................................................. A61F 13/15
(52) U.S. Cl. .............. 604/385.01; 604/358; 604/385.13
(58) Field of Search ...................... 604/385.13, 385.01, 604/358

(56) References Cited

FOREIGN PATENT DOCUMENTS

| | | |
|---|---|---|
| EP | 0745368 A1 | 12/1996 |
| JP | 08-019571 | 1/1996 |
| JP | 08-038547 | 2/1996 |
| WO | WO 97/18784 | 5/1997 |

*Primary Examiner*—A. Vanatta
*Assistant Examiner*—Angela J Grayson
(74) *Attorney, Agent, or Firm*—Darby & Darby

(57) ABSTRACT

Provided is a water-decomposable absorbent article including, a water-decomposable back sheet containing water-dispersible fibers, a water-decomposable absorbent layer, and a water-decomposable surface member for covering the absorbent layer. The outer surface of the back sheet is provided with a plurality of adhesive spots for securing the absorbent article to an external support. The adhesive spots are arranged at intervals both in a longitudinal direction and in a transverse direction. The distance between the neighboring adhesive spots is longer than the maximum fiber length of the fibers constituting the back sheet.

11 Claims, 4 Drawing Sheets

WATER-DECOMPOSABLE ABSORBENT ARTICLE

BACKGROUND OF THE INVENTION

1. Field of the Invention

The present invention relates to a water-decomposable absorbent article for sanitary napkins, pantiliners, incontinence pads, and the like.

2. Description of the Related Art

Recently, absorbent articles of water-decomposable (water-degradable) material have come available, including, for example, sanitary napkins, pantiliners, incontinence pads, and the like. When disposed of in flush toilets, they are dispersed in a large amount of water. Such absorbent articles are disclosed, for example, in Japanese Unexamined Patent Publication (Kokai) Nos. Heisei 8-38547 and 8-19571.

Among the absorbent articles, sanitary napkins, pantiliners and incontinence pads are secured to external supports such as underclothes and diapers so as to prevent them from being displaced or distorted while they are used. For this, an adhesive is applied to the outer surface of the back sheet of the absorbent articles, and the outer surface of the back sheet with the adhesive thereon is to be kept in contact with the external support (the outer surface of the back sheet serves as a garment facing surface).

The adhesive is readily influenced by the moisture existing in the external support and also by the excretions absorbed by absorbent articles, and its adhesiveness may often lower. Therefore, it is desirable that the adhesive for absorbent articles can exhibit good adhesiveness for a relatively long period of time and that the amount of the adhesive applied to absorbent articles is relatively large. However, in case where the adhesive applied to absorbent articles exhibits good adhesiveness for a long period of time and where its amount is too large, the decomposability (degradability) of the absorbent articles will be thereby lowered to a great extent.

When absorbent articles having been disposed of in flush toilets receive a large amount of water, their back sheet shall be degraded in water, but its area coated with an adhesive will decompose more slowly in water than the other area not coated therewith. Specifically, the fibers constituting the back sheet could not be well dispersed in water as they are restrained by the adhesive, and, after all, the back sheet could not be finely dispersed in water. As a result, relatively large pieces of the back sheet not well dispersed in water will float in septic tanks, and they will often clog the pipe lines of septic tanks.

SUMMARY OF THE INVENTION

An object of the present invention is to provide a water-decomposable absorbent article having an adhesive applied onto its back sheet. (the adhesive is for fitting the absorbent articles onto the external supports) and capable of well decomposing in water. The absorbent article is specifically so designed that, when it is in a large amount of water, its back sheet can be pulverized into fine pieces even though the decomposability of the area of the back sheet coated with an adhesive is retarded.

According to an aspect of the invention, a water-decomposable absorbent article may comprise, a water-decomposable back sheet containing water-dispersible fibers, a water-decomposable absorbent layer, and a water-decomposable surface member for covering the absorbent layer, wherein;

the outer surface of the back sheet is provided with a plurality of adhesive spots for securing the absorbent article to an external support, the adhesive spots are arranged at intervals both in a longitudinal direction and in a transverse direction, and the distance between the neighboring adhesive spots is longer than the maximum fiber length of the fibers constituting the back sheet.

On the back sheet of the absorbent article of the invention, the adhesive spot is provided in plural sites, and the distance between the neighboring adhesive spots is longer than the length of the fibers constituting the back sheet. Therefore, in the back sheet, the individual fibers are not in contact with two or more adhesive spots. Accordingly, when the absorbent article is disposed of in flush toilets, the adhesive does not interfere with the decomposability of the back sheet in water. In addition, the adhesive spots in the back sheet are spaced from each other. Therefore, even when some of the adhesive spots are influenced by the moisture existing in the external support or by the excretions absorbed by the absorbent article, all of them are not influenced by them. Accordingly, in its use, the adhesiveness of the back sheet of the absorbent article is hardly lowered.

Preferably, the adhesive spots are provided on the entire outer surface of the back sheet. Also preferably, the adhesive spots are regularly aligned both in the longitudinal direction and in the transverse direction.

Still preferably, an exposed area of the outer surface of the back sheet is continued everywhere between the neighboring adhesive spots, and extends to end edge portions and longitudinal side edge portions.

In the invention, the adhesive spot may be formed of a water-swellable adhesive. For example, it is an acrylic emulsion of particles coated with a hydrophilic protective colloid layer.

The adhesive spot may be also made of a polyvinyl alcohol.

Preferably, the total surface area of the adhesive spots falls between 10 and 30% of the overall surface area of the back sheet.

Also preferably, the maximum length of the fibers constituting the back sheet is at most 4 mm.

Still preferably, the decomposability in water of the, back sheet is at most 300 seconds.

The outer surface of the back sheet may be covered with a release film to protect the adhesive spots, and the release film is preferably decomposable in water.

DESCRIPTION OF THE PREFERRED EMBODIMENTS

The invention will be described hereinafter with reference to the accompanying drawings.

Figure 1:
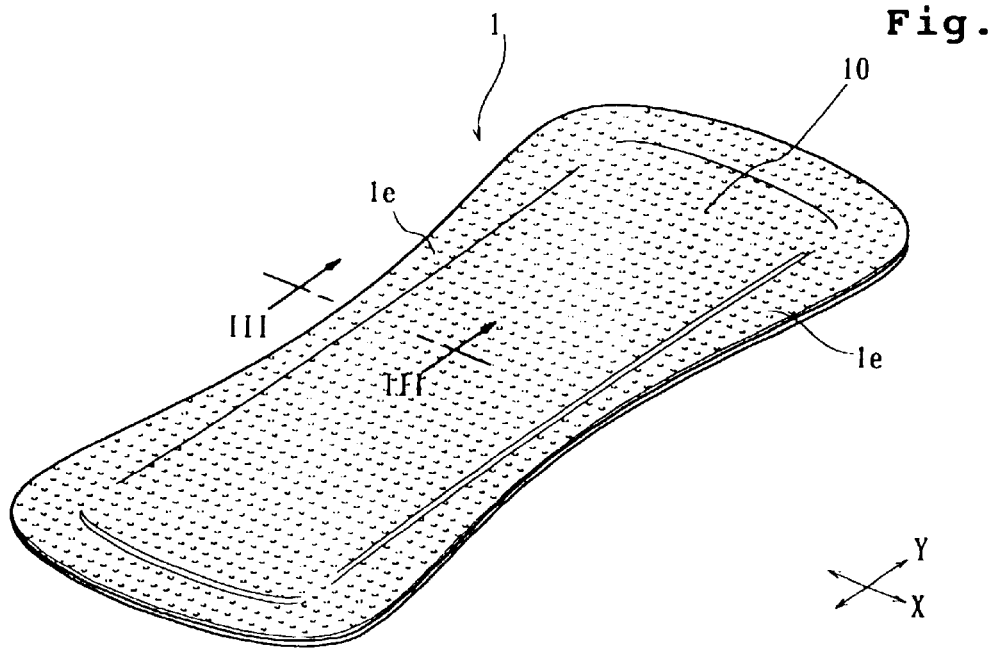
FIG. 1 is a perspective view of one embodiment of an absorbent article of the invention.
Figure 2:
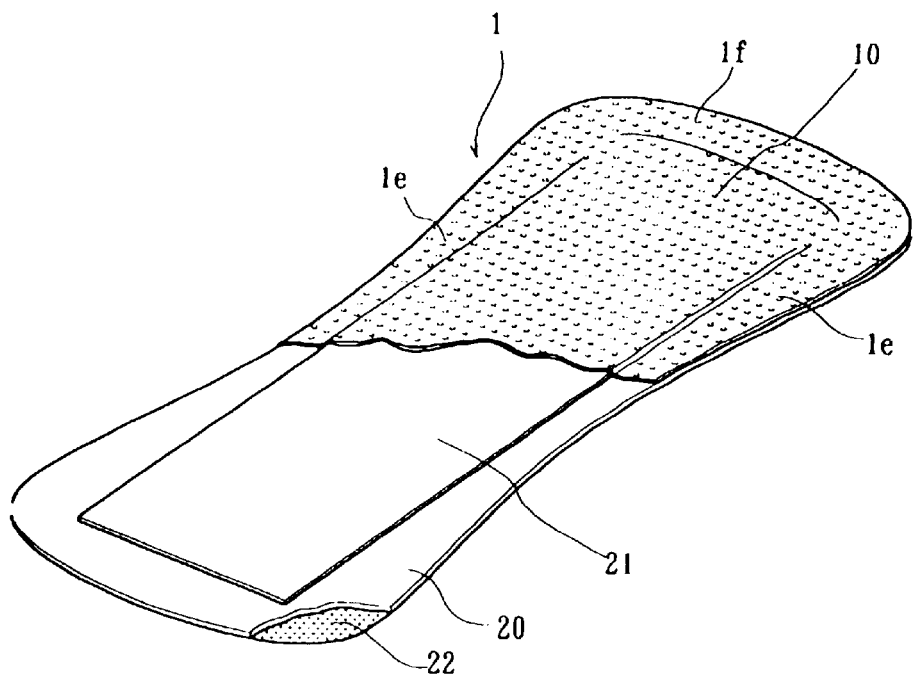
FIG. 2 is a partially cutaway perspective view showing a cross section of the absorbent article of FIG. 1.
Figure 3:
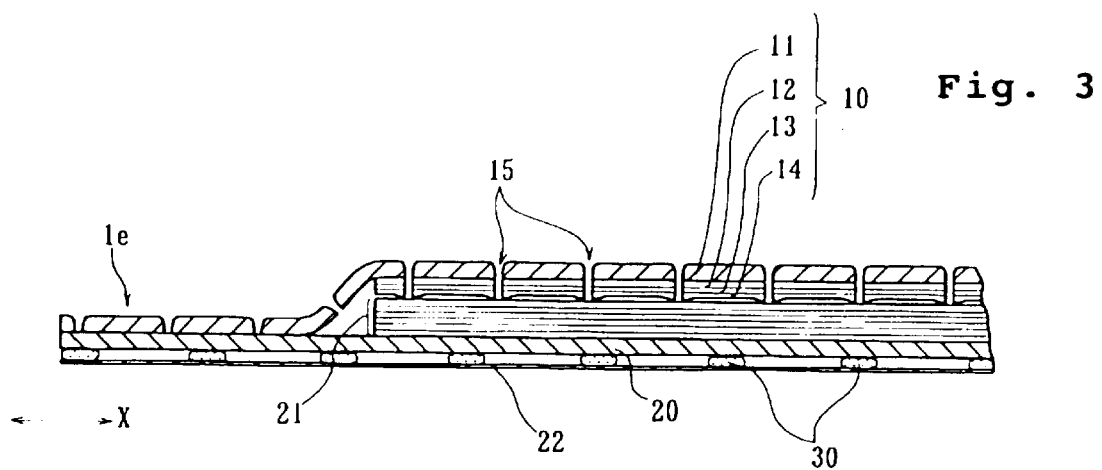
FIG. 3 is an enlarged cross sectional view of FIG. 1, cut along a line of III—III.
Figure 4:
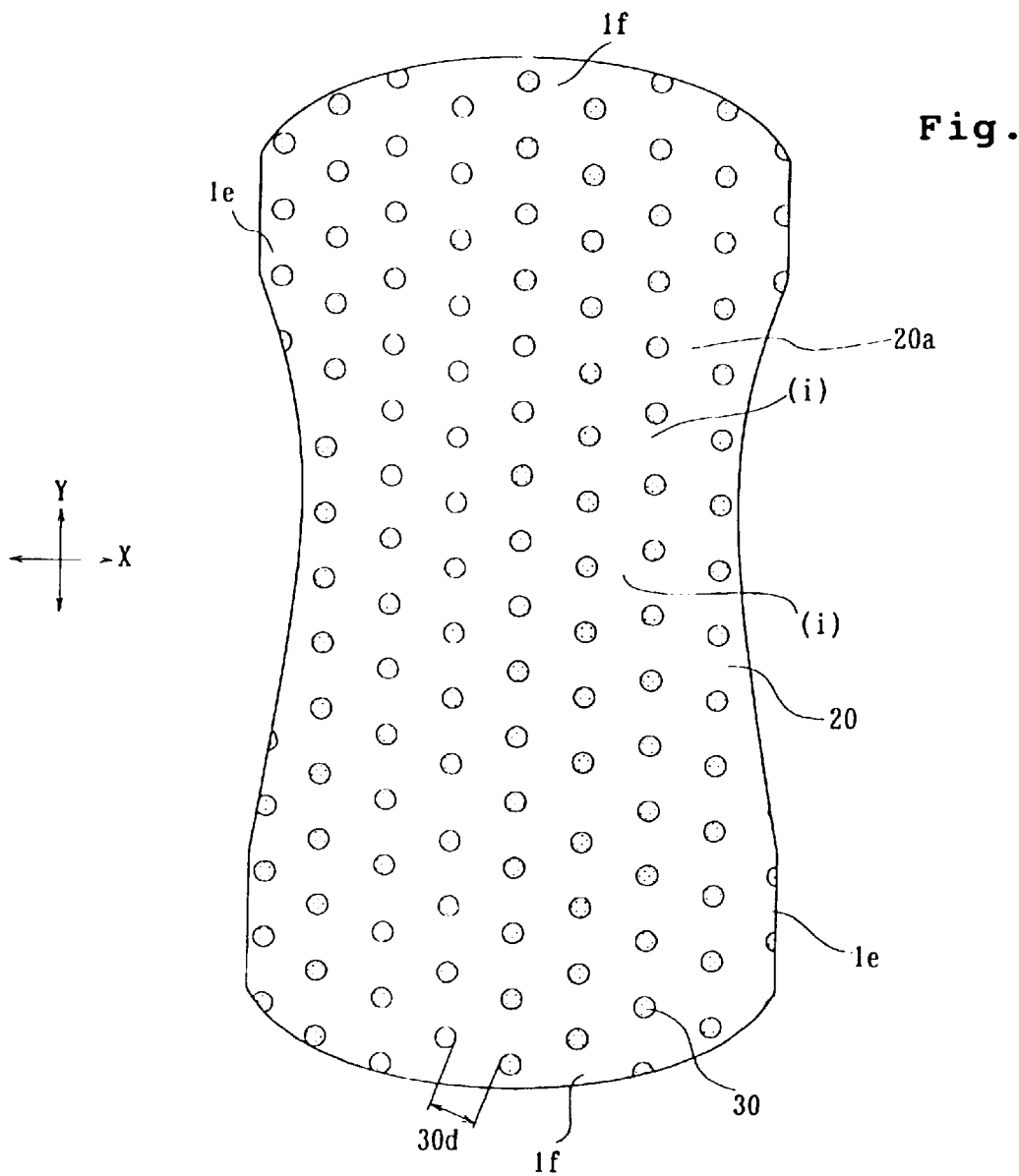
FIG. 4 is a plan view of the outer surface of the absorbent article of FIG. 1, from which the release film has been removed.

FIG. 1 is a perspective view of one embodiment of an absorbent article of the invention, viewed from its top surface (the top surface serves as a body facing surface). FIG. 2 is a partially cutaway perspective view showing a cross section of the absorbent article of FIG. 1. FIG. 3 is an enlarged cross sectional view of FIG. 1, cut along a line of III—III. FIG. 4 is a plan view of the outer surface of the absorbent article of FIG. 1, from which the release film has been removed (the outer surface serves as a garment facing surface). In these, Y indicates a longitudinal direction of the absorbent article illustrated, and X indicates a transverse direction of the absorbent article that is generally perpendicular to the direction Y.

The absorbent article of FIG. 1 is a sanitary napkin or a pantiliner, and this is one embodiment of the water-decomposable absorbent article of the invention.

As shown in FIG. 2, the absorbent article 1 of FIG. 1 comprises a water-decomposable surface member 10 serving as a body facing surface; a water-decomposable back sheet 20; and a water-decomposable absorbent layer 21 sandwiched between the surface member 10 and the back sheet 20. In this, the surface member 10 and the back sheet 20 are bonded to each other with a water-soluble adhesive or the like in the area around the absorbent layer 21 to form longitudinal side edge portions 1e and end edge portions 1f.

As shown in FIG. 4, the back side of the absorbent article 1, that is the outer surface of the back sheet 20 (the outer surface serves as a garment facing surface) has a plurality of adhesive spots 30 applied to the entire outer surface in a polka-dot pattern. As shown in FIG. 3, the absorbent article 1 is preferably provided with a release film 22 which is to protect the adhesiveness of the adhesive spots 30 just before using the absorbent article 1.

Just before the absorbent article 1 is put on, the release film 22 is peeled off. The absorbent article 1 from which the release film 22 has been thus peeled off is applied to the crotch area inside the external supports such as the underclothes and the diapers. In that condition, the absorbent article 1 is secured to the crotch area via the adhesive spots 30 provided on its back side.

In the shown embodiment of FIG. 4, the adhesive spots 30 are circular, preferably having a diameter of from 1 mm to. 10 mm. Apart from the illustrated ones, they may be oval or elliptical, having a longer axis in the direction Y, or may also be in the form of squares or stripes having a width of from 1 mm to 5 mm and a length of from 6 mm to 15 mm. A plurality of the adhesive spots 30 are aligned on the entire outer surface of the back sheet 20 both in the longitudinal direction Y and in the transverse direction X, and they are spaced from each other in the longitudinal and transverse directions. Preferably, the adhesive spots 30 are regularly aligned both in the longitudinal direction and in the transverse direction. These are formed on the entire outer surface of the back sheet 20, extending to the end edge portions If and to the longitudinal side edge portions le, or just before these edge portions 1e, 1f.

An exposed area 20a of the back sheet 20 not having the adhesive spots 30 thereon (the exposed area is referred to as a remaining area except for the adhesive spots 30) is continued in an area (i) between the adhesive spots 30 neighboring both in the longitudinal direction and in the transverse direction, and extends to the end edge portions If and to the longitudinal side edge portions 1e. In other words, the exposed area 20a between the neighboring adhesive spots 30 extends throughout the entire outer surface of the back sheet 20 to reach the end edge portions if and the longitudinal side edge portions 1e thereof, without being interrupted anywhere thereon.

In the shown embodiment of the absorbent article, relatively small adhesive spots 30 are distributed on the entire region of the outer surface of the back sheet 20, and they are spaced from each other therein. Therefore, even when some adhesive spots 30 in some area are influenced by the moisture existing in the external support or by the excretions absorbed by the absorbent article, all the other adhesive spots 30 are not influenced by them. As a result, the adhesiveness of the adhesive spots 30. is hardly lowered while the absorbent article is actually used. In addition, since the adhesive spots 30 are provided on the entire outer surface of the back sheet 20, the absorbent article 1 can be firmly secured to the external support.

When the absorbent article 1 is disposed of in flush toilets and receives a large amount of water therein, water penetrates into the exposed area 20a of the absorbent article 1 through the end edge portions if and the longitudinal side edge portions 1e thereof to degrade the exposed area 20a. As set forth above, the exposed area 20a extends throughout the entire outer surface of the back sheet 20, without being interrupted therein. Therefore, the exposed area 20a is degraded with water everywhere between the neighboring adhesive spots 30, and, as a result, the individual parts each having the adhesive spot 30 formed thereon are separated from each other. Accordingly, after the absorbent article 1 has been disposed of in flush toilets, its back sheet 20 does not remain in septic tanks or the like but is pulverized into small pieces therein.

Specifically, a distance 30d between the neighboring adhesive spots 30 is longer than the maximum fiber length of the fibers constituting the back sheet 20. With that, therefore, when the back sheet 20 is degraded with water in the area (i) between the neighboring adhesive spots 30, the neighboring adhesive spots 30 having been thus separated from each other will be hardly connected with each other by the fibers constituting the back sheet 20. Accordingly, the individual parts each having the adhesive spot 30 formed thereon are more readily separated from each other. For ensuring better degradation of the back sheet in water, it is desirable that the distance 30d between the neighboring adhesive spots 30 is larger than the size (diameter) of the adhesive spots 30.

Preferably, the total surface area of the back sheet 20 occupied by the adhesive spots 30 thereon falls between 10 and 30% of the overall surface area of the back sheet 20. If the area occupied by them is smaller than the lowermost limit of the defined range, the adhesiveness of the adhesive spots 30 required for firmly securing the absorbent article 1 to the external support will be insufficient. On the other hand, if the area occupied by them is larger than the uppermost limit thereof, the distance 30d between the neighboring adhesive spots 30 will be too narrow. If so, water could not easily penetrate into the area (i) between the neighboring adhesive spots 30, and, as a result, the exposed area 20a of the back sheet 20 in that area (i) could not be well degraded with water. With that, after all, degrading the entire back sheet in water will be retarded.

The adhesive for forming the adhesive spots 30 may be any and every one generally used as means for securing absorbent articles. Among them, preferred is a water-swellable adhesive in the form of an aqueous emulsion, for example, an acrylic emulsion of particles coated with a hydrophilic protective colloid layer, etc. Also preferred is a polyvinyl alcohol.

Specifically, the invention is advantageous in case where such a water-swellable adhesive is used. In case where a water-swellable adhesive is used in the absorbent article 1, its adhesiveness will lower little even when it is contacted with the excretions absorbed by the absorbent article 1, and therefore it can all the time ensure the fixation of the absorbent article 1 onto the external support. On the other hand, such a water-swellable adhesive will take relatively a lot of time before it is degraded in water in flush toilets where it is disposed of. Even in such a case, the exposed area 20a in the back sheet 20 of the absorbent article 1 of the invention is readily degraded in water, so that the adhesive spots 30 are separated from each other. Accordingly, even though: the adhesive thereon takes a lot of time before it is degraded in water, the back sheet 20 can be finely pulverized into small pieces in water. In septic tanks, bubbles will adhere onto the adhesive spots and the adhesive-coated pieces of the back sheet will float in water. However, since the size of the adhesive spots 30 is small and since the adhesive-coated pieces of the back sheet are separated from each other in water in septic tanks where the absorbent article has been disposed of, as set forth above, the back sheet is prevented from rising to the surface of water in septic tanks due to the bubbles.

In the embodiment of FIG. 4, the adhesive spots 30 are arranged in a polka-dot pattern to be spaced from each other via the uniform distance 30d therebetween. However, the distance 30d between the neighboring adhesive spots 30 may not be uniform. For their alignment, the adhesive spots 30 may not be aligned at regular intervals but may be aligned at random in any desired manner.

The back sheet 20 is readily dispersed by water jets in flush toilets, or in septic tanks, and it may be made of water-decomposable paper, water-decomposable non-woven fabric or the like that comprises water-dispersible fibers. For example, it may be made of (1) a water-decomposable paper sheet of pulp fibers where the pulp fibers are bonded to each other via hydrogen bonding therebetween, (2) a water-decomposable paper sheet of pulp fibers and other water-dispersible fibers of rayon where the constituent fibers are bonded to each other with a water-soluble binder, (3) a water-decomposable paper sheet of water-decomposable fibers where the constituent fibers are simply entangled, or (4) a water-decomposable non-woven fabric of water-dispersible fibers having a relatively short length where the constituent fibers are forcedly entangled through water-jetting treatment.

Preferably, the outer surface of the back sheet 20 is coated with a water-soluble resin such as a polyvinyl alcohol, an unsaturated carboxylic acid copolymer or the like. Thus coated, the back sheet 20 will be impervious to fluid.

As shown in FIG. 3, the outer surface of the back sheet 20 is covered with a release film 22 to protect the adhesive spots 30 thereon. The release film 22 is made of a water-decomposable sheet of, for example, water-decomposable paper coated with a water-decomposable resin such as polyvinyl alcohol or the like, and its surface is overcoated with a silicone resin or the like. When the release film 22 is attached to the back sheet 20, its silicon resin layer adheres to the adhesive spots 30. Accordingly, the release film 22 can be readily peeled off from the adhesive spots 30, without detracting from their adhesiveness. Furthermore, when the release film 22 is disposed of in flush toilets, its polyvinyl alcohol layer dissolves in water and its water-decomposable paper layer is decomposed and dispersed in water. As a result, the release film 22 itself can be decomposed in water.

The absorbent layer 21 is formed of, for example, water-decomposable paper, pulp or non-woven fabric. In case where the absorbent layer 21 is formed of water-decomposable paper, it is desirable that a plurality of relatively thin, water-decomposable paper sheets are laminated to form it. The absorbent layer 21 thus formed of water-decomposable paper in that manner well decomposes in water. For example, from 4 to 8, preferably 6 or so sheets of water-decomposable papers each having a weight of 14 g/m$^2$ are laminated to form the absorbent layer 21. In case where the back sheet 20 is not processed to be impervious to fluid, the lowermost layer of water-decomposable paper of the absorbent layer 21 may be coated with a water-soluble resin so as to be impervious to fluid. In case where the surface member is thick, the absorbent layer 21 may be omitted.

It is desirable that at least two water-decomposable sheets are laminated to form the surface member 10. For example, as shown in FIG. 3, the surface member 10 has a laminate structure of four water-decomposable sheets 11, 12, 13 and 14. Similarly to the back sheet 20, each water-decomposable sheet may be made of water-decomposable paper or water-decomposable non-woven fabric. With the surface member 10 shown in FIG. 3, the uppermost water-decomposable sheet 11 serving as a body facing surface, is a water-decomposable non-woven fabric of wet-spun lace having a weight of 45 g/m$^2$. The remaining three water-decomposable sheets 12, 13 and 14 are all of water-decomposable paper, each having a weight of 14 g/m$^2$.

The surface member 10 is a laminate of water-decomposable sheets 11, 12, 13 and 14 all integrated by means of wet-dissociative integration ("wet-dissociative integration" means that the integrated constituent sheets are readily dissociated from each other when the surface member is wetted with a large amount of water). As the means of wet-dissociative integration for bonding such a plurality of water-decomposable sheets, there are mechanical means and/or adhesive means and the like. As the mechanical means, the sheets are needled, or are embossed by spotwise pressing them optionally under heat. As the adhesive means, the sheets are partially bonded to each other with a water-soluble adhesive.

With the absorbent article shown in FIG. 3, the surface member 10 is needled for integrating the constituent sheets. Briefly, as shown in FIG. 3, the water-decomposable sheets 11, 12, 13 and 14 are needled under the condition where they have been laminated in that order, in such a manner that the needles could penetrate through them from the top side (which serves as a body facing surface), thereby having through-holes 15 entirely throughout the surface member of the laminate of the sheets. As a result, the fibers constituting each water-decomposable sheet are physically or mechanically entangled around the through-holes 15. With the fibers thus entangled, the plurality of water-decomposable sheets are bonded together to give the surface member 10. In the surface member 10, the through-holes 15 have an additional function of leading fluid to the absorbent layer 21. Preferably, the diameter of the through-hole 15 is at most 3 mm.

In the invention, the back sheet having adhesive spots on its outer surface in the manner specifically defined herein is applicable not only to sanitary napkins but also to pantiliners, incontinence pads, and the like. Preferably, these adsorbent articles are so constituted that they are entirely decomposable in water to be disposed of in flush toilets-and the like, after use.

In case where the absorbent article is provided with wing portions, it is desirable that the back surface of the respective wing portions (the back surface serves as a garment facing surface) is also provided with adhesive spots like the outer surface of the back sheet.

Figure 5:
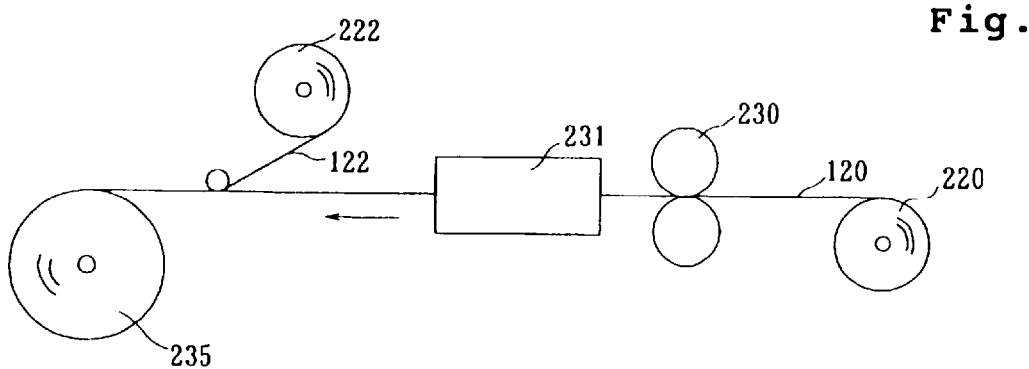
FIG. 5 is an explanatory view showing a process of producing a combined sheet of a back sheet and a release film to constitute an absorbent article of the invention.
Figure 6:
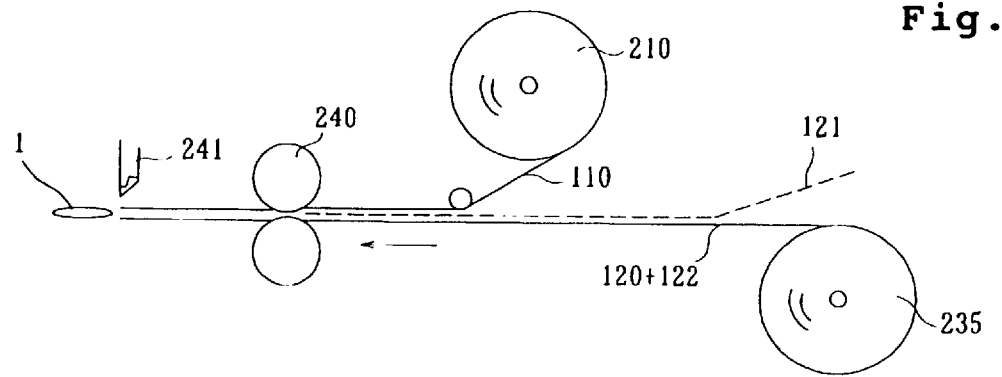
FIG. 6 is an explanatory view showing a process of producing an absorbent article of the invention, in which is used the combined sheet obtained in the process of FIG. 5.

Next, a method for producing the absorbent article of the invention is described. FIG. 5 is an explanatory view showing a process of producing a combined sheet of a back sheet and a release film to constitute an absorbent article of the invention. FIG. 6 is an explanatory view showing a process of producing an absorbent article of the invention, in which is used the combined sheet obtained in the process of FIG. 5.

As shown in FIG. 5, a back sheet strip 120 is fed from a sheet roll 220. One surface (facing upside in the figure) of the back sheet strip 120 thus fed from the sheet roll 220 is spotwise coated with an adhesive by means of a gravure roll 230 to form adhesive spots 30 thereon. Next, the adhesive is dried in a drier 231. In case where the adhesive is an aqueous emulsion such as an acrylic emulsion or the. like, it is dried for a predetermined period of time to increase its adhesiveness.

Next, a release film strip 122 is fed from a release film roll 222 onto the back sheet strip 120 coated with adhesive spots, and the two strips are combined to be a combined sheet strip. The combined sheet strip of the back sheet strip 120 and the release film strip 122 with adhesive spots being sandwiched therebetween is wound up to be a combined sheet roll 235.

In the process of FIG. 5, the back sheet strip 120 and the release film strip 122 may be placed in reverse order. With that, an adhesive is spotwise applied onto the release film strip 122, and the release film strip 122 thus having adhesive spots thereon is laminated with the back sheet strip 120.

Next, the combined sheet roll 235 thus prepared in a production line of FIG. 5 is processed in a different production line, for example, as in FIG. 6. In the production line of FIG. 6, the combined sheet strip, which is composed of the back sheet strip and the release film strip, is fed. from. the combined sheet roll 235. In this stage, the back sheet strip shall face upside, as shown in the figure. With that, an absorbent layer material 121 is fed onto the combined sheet strip, and then a surface member sheet strip 110 is fed from a roller 210 thereover, whereby the absorbent layer is sandwiched between the surface member sheet strip and the combined sheet strip. Next, the surface member sheet strip 110, the absorbent layer material 121, and the combined sheet strip are bonded by a bonding unit 240, and then cut by a cutter 241 into absorbent articles 1 of the invention.

In case where the surface member sheet has a laminate structure comprising a plurality of water-decomposable sheets, the constituent water-decomposable sheets may be previously laminated to form the surface member sheet having a laminate structure, and the laminated sheet strip thus having been prepared separately in a different production line may be fed from the roll 210. On the other hand, the constituent water-decomposable sheets may be laminated in the process of FIG. 6 by feeding them from the respective rolls in order to prepare the laminated surface member sheet, and the thus-prepared, laminated surface member sheet may be directly used in producing absorbent articles 1.

In the shown embodiment, the combined sheet of back sheet and release film is previously prepared in an independent production line separately from the production line for finishing absorbent articles. In this mode, the combined sheet is prepared irrespective of the processing speed in the production line for finishing absorbent articles. Accordingly, in this, it is easy to specifically control the drying time for the adhesive used. In an ordinary method for producing absorbent articles, the products are produced all in one production line. In such an ordinary process, therefore, the drying step for enhancing the adhesiveness of the adhesive used shall be a part of one production line and could not be controlled independently of the other steps in the production line. As a result, the adhesiveness of the adhesive is often poor in the products produced in the ordinary process. As opposed to this, the production process according to the invention is free from such a problem.

EXAMPLES

The invention is described hereinafter in more detail with reference to the following Examples, which, however, are not intended to restrict the scope of the invention.

Using the materials mentioned below, water-decomposable pantiliners were prepared as shown in FIGS. 1 to 4. The water-decomposable non-woven fabric of wet-spun lace used herein for the surface member had a weight of 45 $g/m^2$; and the water-decomposable paper therefor had a weight of 20 $g/m^2$. For the absorbent layer, used was air-laid pulp having a weight of 60 $g/m^2$. For the back sheet, used was.. a water-decomposable non-woven fabric of wet-spun lace comprising rayon and/or pulp fibers, in which the constituent fibers had a length of from 2 to 3 mm. The non-woven fabric had a weight of 30 $g/m^2$. An adhesive was spotwise applied to the outer surface of the back sheet. The distance (mm) between the neighboring adhesive spots on the back sheet, and the area ratio (total surface-area of adhesive spots/overall surface area of back sheet, in terms of %) are given in Table 1. The sanitary napkins thus produced herein were tested for the following matters, and the test data are given in Table 1.

Adhesiveness

The back sheet with adhesive spots thereon is attached to a piece of silk satin, and bonded thereto under pressure by use of a 2-kg roller. Then, using a Tensilon tester, the back sheet is peeled off from the silk satin piece to determine the adhesiveness of the adhesive applied thereto. Expressed in mN, the data are given in the following Table.

Test in Septic Tank

The sanitary napkin is disposed of in a flush toilet, and its behavior in the septic tank is macroscopically observed. The sample tested is evaluated according to the following criteria:

○: The sample disposed of in the flush toilet was degraded in water and deposited in the septic tank.

X: The sample disposed of in the flush toilet gave some floats appearing around the surface of water in the septic tank.

Decomposability in Water

The test for decomposability in water of each sample is based on the water degradability test of JIS P-4501. Precisely, a test piece of the sample having a length of 10 cm and a width of 10 cm is put into a 300-ml beaker filled with 300 ml of ion-exchanged water, and stirred therein with a rotor. The revolution speed of the rotor is 600 rpm. The condition of the test piece being dispersed in water is macroscopically observed at predetermined time intervals, and the time until the test piece is dispersed in water is measured. The sample tested is evaluated according to the following criteria:

○: The sample was degraded in water within 100 seconds.

X: The same was not degraded in water.

The comparative samples are also tested in the same manner as above.

TABLE 1

| | Example 1 | Example 2 | Example 3 | Comp. Ex. 1 | Comp. Ex. 2 | Comp. Ex. 3 |
|---|---|---|---|---|---|---|
| Distance between adhesive spots | 5 | 5 | 5 | 2 | 5 | 5 |
| Area ratio | 12 | 23 | 28 | 28 | 7 | 35 |
| Adhesiveness | 1009 | 1185 | 1538 | 1381 | 196 | 1577 |
| Test in septic tank | ○ | ○ | ○ | ○ | ○ | X |
| Decomposability in water | ○ | ○ | ○ | X | ○ | X |

As is understood from the data in Table 1, the decomposability in water of the absorbent articles is greatly lowered when the distance between the neighboring adhesive spots formed on the back sheet is the same as or smaller than the length of the fibers constituting the back sheet. Furthermore, the absorbent articles disposed of in flush toilets tend to give some floats appearing around the surface of water in septic tanks, when the area ratio of the adhesive spots to the back sheet is larger than 30%.

As described in detail hereinabove, the water-decomposable absorbent article of the invention has adhesive spots formed on the outer surface of its back sheet so as to ensure its fixation to underclothes. When disposed of in flush toilets, its back sheet can be well degraded and finely dispersed in water.

While the invention has been described in detail and with reference to specific embodiments thereof, it will be apparent to one skilled in the art that various changes and modifications can be made therein without departing from the spirit and scope thereof.

Here, 'comprises/comprising' when used in this specification is taken to specify the presence of stated features, integers, steps or components but does not preclude the presence or addition of one or more other features, integers, steps, components or groups thereof.

What is claimed is:

1. A water-decomposable absorbent article comprising, a water-decomposable back sheet containing water-dispersible fibers, a water-decomposable absorbent layer, and a water-decomposable surface member for covering the absorbent layer, wherein;

the outer surface of the back sheet is provided with a plurality of adhesive spots for securing the absorbent article to an external support, the adhesive spots are arranged at intervals both in a longitudinal direction and in a transverse direction, and the distance between the neighboring adhesive spots is longer than the maximum fiber length of the fibers constituting the back sheet.

2. The absorbent article as set forth in claim 1, wherein the adhesive spots are provided on the entire outer surface of the back sheet.

3. The absorbent article as set forth in claim 2, wherein the adhesive spots are regularly aligned both in the longitudinal direction and in the transverse direction.

4. The absorbent article as set forth in claim 1, wherein an exposed area of the outer surface of the back sheet is continued everywhere between the neighboring adhesive spots, and extends to end edge portions and longitudinal side edge portions.

5. The absorbent article as set forth in claim 1, wherein the adhesive spot is formed of a water-swellable adhesive.

6. The absorbent article as set forth in claim 5, wherein the adhesive is an acrylic emulsion of particles coated with a hydrophilic protective colloid layer.

7. The absorbent article as set forth in claim 1, wherein the adhesive spot is formed of a polyvinyl alcohol.

8. The absorbent article as set forth in claim 1, wherein the total surface area of the adhesive spots falls between 10 and 30% of the overall surface area of the back sheet.

9. The absorbent article as set forth in claim 1, wherein the maximum length of the fibers constituting the back sheet is at most 4 mm.

10. The absorbent article as set forth in claim 1, wherein the decomposability in water of the back sheet is at most 300 seconds.

11. The absorbent article as set forth in claim 1, wherein the outer surface of the back sheet is covered with a release film to protect the adhesive spots, and the release film is decomposable in water.

* * * * *